(12) United States Patent
McGrath et al.

(10) Patent No.: US 7,193,054 B2
(45) Date of Patent: Mar. 20, 2007

(54) NANOFABRICATION USING ACTIN FILAMENTS

(75) Inventors: James L. McGrath, Fairport, NY (US); Ian M. Schwartz, Densboro, NY (US); Michael Bindschadler, Rochtester, NY (US); Morton Ehrenberg, Rochester, NY (US); Thomas Gaborski, Rochester, NY (US)

(73) Assignee: University of Rochester, Rochester, NY (US)

( * ) Notice: Subject to any disclaimer, the term of this patent is extended or adjusted under 35 U.S.C. 154(b) by 174 days.

(21) Appl. No.: 10/928,478

(22) Filed: Aug. 26, 2004

(65) Prior Publication Data
US 2005/0106629 A1    May 19, 2005

Related U.S. Application Data

(60) Provisional application No. 60/498,243, filed on Aug. 26, 2003.

(51) Int. Cl.
*C07K 14/00* (2006.01)
(52) U.S. Cl. ..................................... 530/350
(58) Field of Classification Search ............... None
See application file for complete search history.

(56) References Cited

U.S. PATENT DOCUMENTS

| 6,753,038 | B2 | 6/2004 | Fryxell et al. |
| 6,773,616 | B1 | 8/2004 | Chen et al. |
| 2004/0063915 | A1* | 4/2004 | Diner et al. ............. 530/391.1 |

OTHER PUBLICATIONS

Nicolau "Mechanisms for protein micro/nano-patterning on photopolymer substrates," Proc. SPIE, 2000, 3912, 114-9.*
Amann & Pollard "Direct real-time observation of actin filament branching mediated by Arp2/3 complex using total internal reflection fluorescence microscopy," PNAS, 2001, 98, 15009-13.*
Williams et al. "Carbon nanotubes with DNA recognition," Nature, 2002, 420, 761.*
Deng, Zhaoxiang et al.; "DNA-Templated Fabrication of 1D Parallel and 2D Crossed Metallic Nanowire Arrays"; 2003, *Nano Letters*, vol. 3, No. 11, pp. 1545-1548.
Patolsky, Fernando et al.; "Actin-based metallic nanowires as bio-nanotransporters"; 2004, *Nature Materials*, vol. 3, pp. 692-695.

* cited by examiner

*Primary Examiner*—Cecilia J. Tsang
*Assistant Examiner*—Christina M. Bradley
(74) *Attorney, Agent, or Firm*—Townsend and Townsend and Crew LLP

(57) ABSTRACT

The invention provides methods and compositions for using actin for making micro- and nano-scale structures, including masking of two-dimentsional surfaces and non-conductive three dimensional spacers.

34 Claims, No Drawings

NANOFABRICATION USING ACTIN FILAMENTS

CROSS-REFERENCES TO RELATED APPLICATIONS

This application claims the benefit of U.S. Provisional Application No. 60/498,243, filed Aug. 26, 2003, the contents of which are hereby incorporated by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

The ability to manipulate and place materials on a nanometer scale has become important for a number of uses, especially in connection with improving the speed and power use of computer chips and optical devices. The problem of positioning materials over very small distances has been addressed by a number of methods.

Several methods have approached the problems of nanoscale assembly or ordering of compositions by exploiting the self-assembling properties of particular materials. For example, U.S. Pat. No. 6,753,038 discloses the use of self assembling monolayer using precursors such as alkoxysilane, silazane, or chlorosilane on a mesoporous surface, such as silica, using a supercritical fluid. In another approach, U.S. Pat. No. 6,773,616 discloses the use of self-assembling nanowires on a planar surface to serve as an etching mask for fabrication of nanowires of a second composition. The first nanowires may be removed or left. According to the patent, the method enables the formation of one-dimensional crystalline nanowires with widths and heights at the nanometer scale, and lengths at the micrometer scale, avoids traditional lithography methods, minimizes environmental toxic chemicals usage, simplifies the manufacturing processes, and allows the formation of high-quality one-dimensional nanowires over large areas. It would be desirable to have additional methods to provide these benefits.

BRIEF SUMMARY OF THE INVENTION

In some embodiments, the invention provides compositions comprising a surface having disposed thereon (a) an actin nucleation site comprising an isolated actin nucleating agent and (b) an actin capture site comprising an isolated actin capture agent, with a space between said actin nucleating site and said actin capture site. The composition may further comprise a plurality of addressable actin nucleation sites and a plurality of addressable actin capture sites. The composition may comprise at least one actin filament connecting an actin nucleation site to an actin capture site and, if there are a plurality of actin nucleation sites and of actin capture sites, may comprise a plurality of actin filaments connecting the nucleation sites to the capture sites. The surface can be planar. The surface can be silicon, strained silicon, polycrystalline silicon, polycrystalline silicon, silicon dioxide, germanium, gallium arsenic, glass, plastic, ceramic, or metal. The actin nucleation agent can be, for example, ActA, IscA, RickA, a VCA domain, WASp, SCAR, a formin, or a formin FH2 domain. The actin capture agent can be, for example, myosin, N-ethylmaleimide-myosin, phalloidin, α-actinin, or fascin.

In some embodiments, the invention provides a system comprising a surface having disposed thereon (a) an actin nucleation site comprising an isolated actin nucleating agent and (b) an actin capture site comprising an isolated actin capture agent, with a space between the actin nucleating site and the actin capture site The invention further provides a system comprising a first and a second surface, with the first surface having disposed thereon an actin nucleation site comprising an isolated actin nucleating agent and the second surface having disposed thereon an actin capture site comprising an isolated actin capture agent, wherein the system further comprises at least one actin filament connecting said actin nucleation site on the first surface with the actin capture site on the second surface. The first surface and the second surface can be positioned parallel to each other.

In yet further embodiments, the invention provides a method of connecting a pair of points separated by a space on a surface. The method comprises contacting a first point of the pair with an isolated actin nucleation agent, contacting a second point of the pair with an isolated actin capture agent, contacting the isolated actin nucleation agent at the first point with a polymerization solution, which solution comprises ingredients sufficient to induce and to maintain actin polymerization, thereby inducing polymerization of an actin filament; and permitting the polymerization of the actin filament to continue until the actin filament contacts the actin capture agent at the second point, thereby connecting said first and second points. The method can further comprise immersing the first point, the second point, and the space between the points with the polymerization solution at the same time. The polymerization solution can be removed following the contacting of the actin filament to the second point. A fixative can be added to the polymerization solution following the contacting of the actin filament to the second point. The actin filament can optionally be coated with a substance after the polymerization solution is removed from said actin filament. The surface can further be coated with a non-stick coating before contacting the actin nucleation agent on the first point with the polymerization solution. The actin nucleation agent can be selected from the group consisting of ActA, IscA, RickA, a VCA domain, WASp, SCAR, a formin, and a formin FH2 domain. The actin capture agent can be selected from the group consisting of myosin, N-ethylmaleimide-myosin, phalloidin, α-actinin, and fascin. The method can further comprise a plurality of pairs of points on said surface. The plurality of pairs of points on the surface can be arranged in an addressable array. The surface can be contacted with an etching solution following the formation of the actin filament. A particle may be attached to the polymerizing actin filament to permit a force to be exerted to direct the filament towards the actin capture agent. The particle can be a magnetic particle. A magnetized substance can be positioned near the magnetic particle to draw said magnetic particle towards the actin capture agent. The particle can be a transparent or translucent particle, and the filament can be directed towards the actin capture agent by optical gradient pressure. The method can include directing the polymerizing actin filament towards the actin capture agent by flowing the polymerization solution toward the actin capture agent. The surface can be silicon, strained silicon, polycrystalline silicon, polycrystalline silicon, silicon dioxide, germanium, gallium arsenic, glass, plastic, ceramic, or metal. The said surface can be planar.

In another set of embodiments, the invention provides methods for forming three dimensional actin structures. The methods comprise providing a first surface having a first point, which first point has thereon an actin nucleation agent and a second surface having a second point, which point has thereon an actin capture agent, and further wherein said first and said second surfaces are positioned so as to create a space of up to 10 microns between the surfaces; filling the space between the first point on the first surface and the second point on the second surface with a polymerization solution, which solution comprises ingredients permitting induction and maintenance of actin polymerization, thereby inducing polymerization of an actin filament; and permitting the polymerization of the actin filament to continue until the actin filament contacts the actin capture agent at the second point, thereby connecting the first and second points; thereby creating a three dimensional structure. The first and second surfaces may be positioned parallel to each other. The methods may further comprise a plurality of points on the first surface to be connected to a plurality of points on the second surface. The method may further comprise separating the first and second surfaces to exert a tension on the actin filament until a desired separation between the surfaces is achieved. The surfaces can be independently selected from the group consisting of silicon, strained silicon, polycrystalline silicon, polycrystalline silicon, silicon dioxide, germanium, gallium arsenic, glass, plastic, ceramic, and metal. A particle may be attached to the polymerizing actin filament to permit a force to be exerted to direct the filament towards the second site on the second surface. In some embodiments, the particle is magnetic. The actin filament may be released from the first surface by contacting the filament with capping protein.

In still embodiments, the invention provides methods of patterning a surface with a substance. The method comprises providing an isolated actin filament on the surface in the desired pattern, coating the surface with a protein other than actin, depolymerizing the actin filament, and removing the depolymerized actin and protein coating the actin, coating the surface with the substance to be patterned, applying a protease to remove the protein other than actin, and removing the protein other than actin and substance coating it, thereby leaving on the surface the substance in the desired pattern.

DETAILED DESCRIPTION OF THE INVENTION

Introduction

Actin is the most abundant protein by weight in animal cells. It is a highly conserved protein and is one of the most studied of all proteins. Surprisingly, we have now discovered that the properties of this biological molecule can be exploited to provide methodologies for fabricating structures on scales ranging from micrometers to nanometers. We have discovered, for example, that actin can be used to form the scaffolding or structure for microscale and nanoscale devices or components, and can manipulated to form structures from point to point on a surface, such as on a planar surface. Moreover, the points can be two desired points on a surface, permitting the assembly of structures in an ordered fashion.

Even more surprisingly, it has been discovered that actin can be manipulated to form a three dimensional structures. Further, it has been discovered that actin can be used to form structures as thin as the diameter of a single actin filament (approximately 7–8 nanometers) to thicker structures comprised of bundles of actin filaments (e.g., 90–100 nanometers). Additionally, structures with multiple filaments can be shaped to form, for example, columns. Thus, the present invention provides methods and compositions for forming a variety of ordered structures on the micron and nanometer scale for manufacturing and other purposes.

As noted above, actin is one of the most studied of all proteins, and its polymerization has been studied for almost fifty years. Actin is a monomeric globular protein ("G-actin") which can polymerize to form filaments of filamentous actin ("F-actin") (the forms of actin are discussed in more detail in a later section). G-actin monomers tend not to associate with each other, but rapidly associate with and assemble into a polymerizing filament once at least three monomers have polymerized. The initiating events of actin polymerization, and the conditions under which it does and does not occur have been carefully studied over the years, and the discussion herein will emphasize certain relevant aspects, with the understanding that persons of skill in the art are aware of the many detailed teachings in this area regarding such matters as the components necessary to permit actin polymerization and the conditions needed for it to occur.

Once started, actin polymerization proceeds rapidly so long as a sufficient concentration of G-actin, ATP, and divalent cations are present. G-actin monomers tend to polymerize into a filament rapidly once three monomers have assembled into an initial polymer of three F-actin molecules. The presence of a dimer of F-actin, or of a molecules that mimic the appearance of such a dimer, increases the chance that a G-actin monomer will reach and interact with the dimer or mimetic and initiate the polymerization.

There are several pathways by which actin polymerization can be initiated. The best studied involves the presence of a conserved seven protein complex known as the actin related protein ("Arp") 2/3 complex. When acted upon by certain agents, such as the *Listeria monocytogenes* protein ActA, the conformation of the Arp2/3 complex changes and resembles two polymerized F-actin molecules. The complex can then recruit a G-actin monomer, and convert it to an F-actin form. The Arp2/3 complex-F-actin combination then appears to G-actin monomers as a three F-actin filament, and nucleates rapid F-actin polymerization. See, e.g., Welch et al., *Science*, 281:105–8 (1998).

A number of agents are known which can serve to change the conformation of the Arp2/3 complex. Many of these are bacterial proteins, such as ActA. As noted, it is the Arp2/3 complex that actually nucleates the polymerization of actin; the agents activate the complex by changing its conformation to resemble an F-actin dimer. These agents are therefore indirect nucleating agents. Further, some agents that initiate actin polymerization through the Arp2/3 complex do not interact with the complex directly. For example, Cossart, *Cellular Microbiol* 2(3): 195 (2000), observes that the *Shigella* protein IcsA recruits N-WASp and activates it in a Cdc42-like fashion. This activation leads to Arp2/3 complex recruitment, activation of the complex and ultimately actin polymerization.

Actin polymerization can also be initiated in an Arp2/3-independent manner. See, e.g., Fradelizi et al., *Nature Cell Biol.*, 3:699 (2001). For example, a family of proteins known as "formins" do not need Arp2/3 to nucleate actin polymerization. Like the Arp2/3 complex, the formins initiate actin polymerization by resembling a dimer of F-actin; unlike the Arp2/3 complex, the formins do not appear to need a conformational change before they will initiate actin polymerization, and therefore do not need to be activated by some other agent. Thus, they can be considered direct nucleating agents of actin polymerization. When formins or formin domains with actin polymerization activity, such as the FH2 domain, are used to initiate actin polymerization, accordingly, the polymerization solution does not need to include the Arp2/3 complex.

As noted above, ActA and other agents that activate the Arp2/3 pathway are indirect nucleation agents, while formin and the FH2 domain of formin are direct nucleating agents. For ease of reference herein, however, agents that are capable of initiating actin polymerization, either directly or by changing the conformation of the Arp2/3 complex to induce actin polymerization, will be referred to herein as "actin nucleating agents" or "nucleating agents" unless otherwise required by context. With respect to those agents which work through the Arp2/3 complex pathway, changing the conformation of the Arp2/3 complex to initiate actin polymerization will be referred to as "activation" of the Arp2/3 complex for ease of reference.

Among its unusual properties, actin continues to polymerize from around the initial nucleation site. Thus, actin filaments are directional, with two ends. Conveniently, actin can be thought of as being extruded, or extending, from the site at which it is nucleated. The actin end that is distal to the nucleation site is commonly referred to as the "pointed" or "minus" end, while the end proximal to the nucleation site is commonly referred to as the "barbed," or "plus" end. The polymerized actin filament is composed of two protofilaments, and the composite structure resembles a tightly wound double helix.

A. Connecting Points on a Surface

In some embodiments of the invention, actin filaments are used to connect two points on a surface. In some embodiments, the surface can be considered to be flat or planar, although the methods of the invention can be used on curved or otherwise shaped surfaces. In a typical application, the two points are selected, and an actin nucleating agent is applied to the first point (which can conveniently be referred to as the "nucleating" site or point).

A second agent, this one having an affinity for F-actin, is applied to the second point (which can conveniently be referred to as the "actin capture site" or "actin capture point" or simply the "capture site" or "capture point"). The agent with an affinity for F-actin can be considered as the "actin capture agent" or, more simply, the "capture agent." The exemplar capture agent is myosin. If myosin is used as the capture protein, it can optionally be treated with n-ethylmaleimide ("NEM"), which will cause the myosin to irreversibly bind the actin. (Sheetz, M. P., et al., ATP-dependent movement of myosin in vitro: characterization of a quantitative assay. *J Cell Biol.* 99:1867–71 (1984)).

The surface is then contacted with a solution that contains the ingredients known in the art to be required for actin polymerization, such as Arp2/3 complex, ATP, ions, and an appropriate concentration of G-actin monomers, under conditions of temperature and the like conducive to such polymerization. Actin filaments will then polymerize and extrude from the nucleation site until one or more reach the site containing the capture protein. The directionality of the filaments will usually be unimportant, but it can, of course, be controlled if desired by placing the nucleation point and the capture point so that the filament or filaments run from the nucleation point to the capture point in the preferred direction.

If desired, the nucleation sites and capture sites can be patterned by any of a number of techniques such as microcontact printing, photolithography, laser ablation, or additive (Ginger et al., "The evolution of dip-pen nanolithography," *Angew Chem Int Ed Engl*, 43:30–45 (2004)), or subtractive nanolithography techniques (Wadu-Mesthrige, et al., "Fabrication of nanometer sized protein patterns using atomic force microscopy and selective immobilization", *Biophys J* 80:1891–9 (2001)). For example, for structures on the order of micrometers, micropatterning of the work surface by contact printing can be accomplished by pressing the work surface against a micropatterned stamp coated with the nucleating protein. This is be followed by microcontact with a second, differently-configured stamp that patterns the capture protein. Alternatively, both the nucleating agent and the capture agent can be on the same stamp so that both are placed on the surface in a single contact. Stamps for protein deposition are typically made using photolithography on polydimethylsiloxane ("PDMS") substrates following what is now standard practice. The stamp can be 'inked' directly with the protein which will be either passively adsorbed, or may be covalently bound to the substrate using common procedures. See, e.g., Degenhart, G., et al., Micro- and nanofabrication of robust reactive arrays based on the covalent coupling of dendrimers to activated monolayers. *Langmuir.* 20:6216–24 (2004); Feng, J., et al., A novel process for inking the stamp with biomacromolecule solution used in reactive microcontact printing. *Colloids and Surfaces B: Biointerfaces*, 36:177–180 (2004).

Complex networks can be created by, for example, repetitive processes in which pairs of nucleating and binding patches are created, followed by a round of polymerization. The speed of creating the patterns can be accelerated by adding molecules that enhance polymerization, such as the protein profilin or the fungal metabolite phalloidin.

Multiple nucleation points and capture points may be positioned on a surface. Ordered arrays of filaments can be provided by, for example, placing a series of nucleation points and capture points in a desired pattern, so long as the points are sufficiently separated on the surface so that the filament or filaments from one nucleation site do not reach the capture site for another member of the array. The distance to separate pairs of nucleation and capture points can be readily determined.

The formation of the desired pattern can be enhanced by first coating the surface with a substance that reduces non-specific binding of the actin filaments to the surface. A number of substances are known in the art to be suitable for reducing non-specific binding to a surface. In a preferred embodiment, the substance is a protein or composition comprising protein that is compatible with the intended application. Proteins and compositions commonly used in immunology assays to reduce non-specific binding, such as non-fat milk, bovine serum albumin, and human serum albumin, are typically useful for the applications of the invention. If non-protein substances are desired, a number of non-stick substances such as silanes that have not been derivatized with functional groups can be used. Alternatively, the surface can be coated with polyethyleneglycol, potentially as part of a self assembled monolayer. (Prime and Whitesides, *Science* 252:1164–7 (1991)). For patterning on nanometer scale dimensions, various methods from nanolithography can be used, such as Dip Pen (Ginger 2004, supra), Atomic Force Microscopy ("AFM") subtraction (Wadu-Mesthrige et al., 2001, supra), and plasma deposition.

It is desirable that the nucleation site and the capture site are free of the non-stick coating. There are a number of ways of accomplishing this. For example, if the nucleating agent and capture agent are applied and the non-stick coating is then applied, the nucleation site and capture site will be free of non-stick coating. Second, the sites can be covered with a removable material prior to contacting the surface with the non-stick coating. The material is then removed, leaving the sites free of the coating. Third, and perhaps most conveniently, spots free of the coating material ("bald spots") are created at the nucleation site and the capture site by removing the coating at the sites. The coating material can, for example, be burned off with a laser, or scraped or pushed away using an AFM needle used in contact mode.

The precision of constructing the actin scaffold or structure can be further improved by manipulating the polymerizing actin filament or filaments in the desired direction to lead them directly to the capture site. Conveniently, the polymerizing actin filament or filaments are guided by connecting the filament or filaments to magnetic particles, such as magnetic beads, which can then be guided towards the capture site by attracting them with a magnetized instrument or appropriately sized magnet. The particles are desirably attached to the barbed end of the filament or filaments; attachment can be accomplished using routine conjugation chemistry known in the art, such as the chemistries taught in Hermannson, G., *Bioconjugate Techniques*, Academic Press, San Diego, Calif. (1996), or by coating the particles with anti-actin antibodies or with fragments of such antibodies that retain antigen recognition ability. Typically, the magnetic particles beads are connected to the filament or filaments soon after the polymerization has begun.

Alternatively, a translucent or, preferably, a transparent particle, such as a bead, is attached to the polymerizing actin filament or filaments. These particles can be attached to the actin filament by the same conjugation technologies as mentioned above. Force can be exerted to direct the filament or filaments to the capture site by laser-induced optical gradient forces (Ashkin, Methods *Cell Biol* 55:1–27 (1998)) applied to the particles bound to the filaments (Rock, R. S., et al., In vitro assays of processive myosin motors. *Methods.* 22:373–81 (2000)).

The surface can generally be any surface used for microscale or nanoscale applications, such as silicon, strained silicon, polycrystalline silicon, polycrystalline silicon, silicon dioxide, germanium, gallium arsenic, glass, plastic, ceramic, or metal. In some applications, the actin filament may protect a portion of a top layer of a multi-layered composition, permitting portions of the top layer not protected by the actin filament to be removed, such as by etching the unprotected portions away. It should be noted that a large body of technology has been developed for masking and etching surfaces, and for depositing materials on surfaces, including physical deposition, molecular beam epitaxy, sputtering, and chemical deposition has been developed in connection with the semiconductor industry over the past two decades, see, e.g., McGuire, G. E., ed., Semiconductor Materials and Process Technology Handbook, William Andrew Publishing/Noyes (1988); D. A. Glocker & S. I. Shah (Eds), Handbook of Thin Film Process Technology, Institute of Physics Publishing (1995), K. Wasa et al., Thin Film Materials Technology: Sputtering of Compound Materials, William Andrews Publishing, Norwich, N.Y. (2004), and can be used in connection with the compositions and methods provided by the invention.

The actin filament can then be left in place or removed, as desired. In some embodiments, the actin can be carbonized or burned off by heating the surface.

While beads can be used to direct the filament towards the capture site, as described above, preferably the surface on which the actin is forming a pattern or structure is not a bead. In some embodiments, the methods of the present invention contemplate that either the same surface will be provided with both a nucleating agent, such as ActA, and a capture agent, such as myosin, or that there will be two paired surfaces, one with the nucleating agent and the other with the capture agent, so positioned so that an actin filament can polymerize therebetween. In some embodiments, a plurality of nucleation sites will be present, with a corresponding plurality of capture sites. The plurality of either or both of the nucleation sites and the capture sites can be in an addressable array.

For forming a 2 dimensional structure, the two surfaces to be connected will typically be adjacent to and in line with each other. Formation of three dimensional structures is discussed in the next subsection.

Once the actin has provided a structure or scaffold, it can, for example, serve as a mask to cover the surface while the surface not covered with the actin is etched. For example, in chip manufacturing, a thin metal film is typically deposited on a semiconductor, such as silicon, the metal is masked in a desired pattern, and the non-masked metal is etched away. The methods of the present invention permit masking a desired pattern on the metal layer with one or more actin filaments, and then etching the metal not masked by the actin filament or filaments.

Conventional etching agents for surfaces can be used Typically, even agents that will destroy the actin filament and commence to etch the surface underneath the filament will do so only with a time lag between commencing to etch the unprotected surface and getting through the actin to etch the surface below. Thus, by removing the etching solution before the solution has etched through the entirety of the actin filament, the methods of the invention can be used to etch patterns on surfaces even with solutions that would etch or degrade the actin. The time in which any given etching substance can be permitted to etch the surface without degrading the actin and commencing to etch the surface below can be determined empirically by routine experimentation by simply running replicates using increasing amounts of time for each replicate until etching of the surface under the actin filaments is observed. Following etching, the actin can be removed to reveal the unetched surface, or left in place.

In another group of embodiments, the actin can be coated with a second substance. In its simplest embodiment, the actin and the surface on which it is formed can be coated with a substance. In another embodiment, the actin can be coated with a substance that deposits preferentially on the actin, which is slightly raised compared to the surface on which it has polymerized, or by a method which will preferentially deposit the substance on a raised surface. In yet another embodiment, if the surface has been coated with a non-stick substance prior to formation of the actin filaments, as described above, and if the non-stick substance is not removed, the actin can be coated with a substance that sticks to the actin but not to the non-stick coating, permitting the actin to serve as a pattern for the material coating the actin. Once covered, the actin can be left in place, or removed. For example, if the surface and the material deposited on the actin are not harmed by heating, typically, the actin is effectively removed by heating the surface to a temperature that will effectively carbonize the actin.

Individual actin filaments can act as a positive mask for substance deposition in manufacturing. After actin filaments have been formed in the desired orientation on the substrate, a second protein (actin may be considered as the first protein on the surface), one susceptible to proteolytic degradation, is deposited onto the surface. The actin filaments mask the surface from the coating provided by the second protein. Then, an actin specific protein, such as gelsolin, depolymerizes the actin filaments so they can be removed from the surface, along with any of the second protein that has coated the filaments. Conveniently, the depolymerized actin is removed by gently washing the surface. The second protein will generally adhere to the surface it coats without having depolymerized actin underneath the second protein. A substance of choice is then deposited over the entirety of the surface, in a layer thin enough to permit a proteolytic enzyme access to the second protein. Finally, a proteolytic enzyme (a protease) degrades the second protein, allowing removal of the substance of choice where it has coated the second protein. What will remain is a coating of the substance of choice in the pattern originally formed by the actin filaments. The substance of choice can be patterned on the surface to the width of a single actin filament (7–8 nm).

B. Three Dimensional Structures

The invention further provides methods for forming three dimensional forms using actin filaments. In one set of embodiments, two surfaces are positioned with one just over the other. One of the surfaces, conveniently the bottom surface, has one or more sites on which is positioned an agent with the ability to activate the Arp2/3 complex to initiate actin polymerization, as described above (the "nucleating agent"). The second surface has one or more sites on which is positioned a protein with an affinity for F-actin, such as myosin (the protein with affinity for F-actin may conveniently be referred to as the "capture protein"). Preferably, the two surfaces are positioned about 10 nanometers to about 1 micron apart, to permit G-actin monomers between the surfaces to interact with the nucleating agent. The space between the two surfaces is filled with a solution comprising ATP, and the other components known in the art to be required for actin polymerization (including Arp2/3 complex, if ActA or another agent which acts through the Arp2/3 pathway is used as the nucleating agent), under conditions known in the art to be conducive to permitting polymerization to occur. As the nucleation occurs and filament polymerization commences, the second surface is initially positioned close to the first surface, permitting the distal end of the polymerizing filament to contact the capture agent, such as myosin. If desired, the distal end can be directed towards the capture agent by any of a variety of means, including inducing a flow of the polymerization solution in the direction from the nucleating agent to the capture agent, or by attaching particles to the actin filament, as described above, and then exerting forces on the particle, thereby exerting force on the filament which directs it towards the capture agent. For example, a magnetic particle can be attached to the filament, which is then drawn towards the capture agent by positioning a magnet behind the surface bearing the capture agent or, space permitting, between the end of the filament and the capture agent.

Once the filament has attached to the capture agent, the surfaces are separated at a speed commensurate with the rate of polymerization expected given the temperature and reagent conditions employed. Mechanisms for separating two surfaces or for moving a single surface are known in the art. (See, e.g., Marcy, Y., et al., Forces generated during actin-based propulsion: a direct measurement by micromanipulation. $Proc\ Natl\ Acad\ Sci\ U\ S\ A$. 101:5992–7 (2004)). The separation permits the polymerizing filament to extrude from the nucleation site while maintaining contact with the capture site. It is anticipated that the procedure will permit the generation of quite long actin filaments, of 200, 400, 500, or even 1000 microns. However, it is anticipated that many uses of the filaments made by this process will require filaments only on the order of 5–10 microns.

While a three dimensional structure can be of a single actin filament, more commonly these applications will involve a plurality of filaments. Conveniently, if multiple nucleation and capture sites are arrayed on two flat surfaces, and the surfaces are maintained parallel relative to each other, the procedure described above will result in the formation of nanoscale actin filament structures that are of equal height. By ordering the nucleation sites and capture sites in ordered arrays, such as the addressable arrays commonly used in manufacturing chips for gene analysis (such as the Affymetrix "GeneChip,®" the methods just described permit the generation of ordered arrays of nanostructures of equal height.

By increasing the size of the nucleation site, the number of the actin filaments polymerizing from the site can be varied from lesser to greater as desired, with the diameter of the column of actin filaments consistent with the diameter of the nucleation site. A small nucleation site will provide room for the nucleation and polymerization of only a few actin filaments, while a larger site will initiate the polymerization of a larger number. The shape of the structure can also be varied. A round or a square nucleation site will result in actin filaments polymerizing to form a column of actin filaments approximating the shape in which the nucleating protein was placed on the first surface.

If it is desirable to increase the structural strength of the actin column, the column can be strengthened by the use of proteins known in the art to cross-link actin filaments. Numerous proteins are known that bind, bundle, or cross-link actin filaments in cells, as noted further below. The exemplar binding protein is fascin, which can be used to link each subunit in one filament with a subunit in a neighboring filament. (Matsudaira, P. Actin crosslinking proteins at the leading edge. $Semin\ Cell\ Biol$. 5:165–74 (1994)). Similarly, the protein α-actinin can be used to link filaments. Both fascin and α-actinin line the filaments in parallel and link the filaments, but fascin links them more tightly. Fascin is therefore preferred where both column uniformity and strength is desirable. Use of these and other linking proteins known in the art is easily accomplished by washing or immersing the actin structures in a solution comprising an excess amount of the linking protein or an amount roughly equimolar with the amount of actin present.

Current polymers used in manufacturing cannot readily be disassembled. In contrast, actin columns can be disassembled by the proteins cells use to regulate actin. A unique structural property of actin columns is their reversibility. Thus, actin columns have a significant and surprising advantage over the currently-available materials for micro- and nano-scale fabrication and structure.

This property can be used to alter and optimize the spatial properties of three dimensional micro- and nano-structures. For example, the actin columns can be used as non-conductive spacers between two plates to form a micro- or nano-scale capacitor. A feedback loop is designed such that the growth reaction is halted upon reaching the proper displacement. Unique to actin columns, this displacement can be controllably increased with further polymerization or decreased via depolymerization. The reversible nature of actin polymerization allows for spatial optimization of micro- and nano-structures that can be directly related to electrical and other material properties.

After the filament column or columns have been formed, they can be left attached to the surfaces. Alternatively, if it is desired that the columns are attached to only one surface, with one end of the column free, the columns can be detached at the barbed end by use of a protein known as "capping protein". Recombinant capping protein is known in the art. See, e.g., Soeno, Y., et al., *J. Muscle Res. Cell Motil.* 19:639–646 (1998).

Actin columns are particularly useful as structural components in devices to be disassembled on command. They can be disassembled, for example, to prevent unauthorized access to information in devices containing, for example, proprietary, classified, or military information. One particular use is in logic devices.

Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

Actin was discovered over 50 years and has been extensively studied. Actin monomers assemble to form filaments that are composed of two proto-filaments and that appear as a tightly wound double helix upon microscopic examination. The filaments have a diameter of approximately 7–8 nanometers.

"ActA" is a protein of the bacteria *Listeria monocytogenes*. It promotes Arp2/3-dependent actin nucleation. Two domains of ActA (residues 85–104 and 121–138) with sequence similarity to WASP homology 2 domains bind two actin monomers with submicromolar affinity. ActA binds Arp2/3 with a K(d) of 0.6 mM. The minimal Arp2/3-binding site of ActA (residues 144–170) is C-terminal to both actin-binding sites and shares sequence homology with Arp2/3-binding regions of WASP family proteins. As used herein, reference to "ActA" refers to the full length ActA protein, to a portion of ActA (such as the sequence of residues 144–170) that binds Arp2/3), or to a mimetic of either of these, unless otherwise required by context.

The "Arp2/3 complex," first isolated from *Acanthamoeba castellani*, consists of seven polypeptides; two actin-related proteins, Arp2 and Arp3; and five other proteins, p40, p35, p19, p18, and p14. The human complex consists of seven subunits that include the actin related proteins Arp2 and Arp3, and five others referred to as p41-Arc, p34-Arc, p21-Arc, p20-Arc, and p16-Arc. The predicted amino acid sequence of all seven subunits has been determined. Studies have determined that the nucleating and organizing activities of the complex are separable. Thus, not all the subunits of the Arp2/3 complex may be necessary for the nucleation activity contemplated by the methods of the invention. Accordingly, as used herein, references to the "Arp2/3 complex" refer to the full 7 component complex, or to assemblages of such components of the complex as are necessary to nucleate actin polymerization, unless reference to the full 7-protein complex is required by context.

"WASP" refers to the Wiskott-Aldrich syndrome protein family. Wiskott-Aldrich syndrome (WAS) is a rare X-linked disease, and the WAS protein (WASp) is the founding member of a protein family that are considered activators of the Arp2/3 complex. See, e.g., Thrasher, *Nature Reviews Immunol.*, 2:635–646 (2002). The WASP family of proteins currently consists of five members: WASp, N-WASp, Scar-1, and three WAVE isoforms. WASP homolog N-WASP is expressed ubiquitously in vertebrate cells. See, e.g, Alto et al., *Diabetes* 51:S385–S388, 2002. Three mammalian orthologs of Scar-1, termed WAVE-1, WAVE-2, and WAVE-3, have been cloned. Id.

"VCA" (verprolin-homology, cofilin-homology, acidic regions) refers to a domain of WASP proteins that constitutively activates Arp2/3 complex. The domain has been cloned and has been recombinantly expressed and used to induce actin polymerization in studies. See, e.g., Bernheim-Groswasser et al., *Nature*, 417(6886):308–11 (2002).

"Phalloidin" is a fungal toxin from *Amanita phalloides* that binds actin. E.g., Löw, I. & Wieland, T., *FEBS Letters*, 44:340–343 (1974). It is specific for F-actin and binds at the junction between subunits. E.g., Steinmetz, M. O., et al., *J. Mol. Biol.* 276:1–6 (1998).

"N-ethyl-maleimide," or "NEM," is a chemical that, when reacted with myosin, converts the myosin to a form that irreversibly binds actin.

Actin

Actin is the most abundant protein in animal cells and comprises 10 percent by weight of the total cell protein of muscle cells and 1–5 percent of the cellular protein of non-muscle cells. Actin molecules each bind an ATP molecule and self-assemble into long, two-stranded filaments during which the ATP is hydrolyzed into ADP. Actin is a 375 residue, 43 kD protein, encoded by a large, highly conserved gene family. As described by Lodish et al., Molecular Cell Biology, W. H. Freeman & Co., actin is among the most highly conserved of proteins. In vertebrates, there are several isoforms: the a isoform or isoforms are present in various muscle cells and the β- and γ-actin isoforms are present in nonmuscle cells. The isoforms differ at only a few positions, located primarily in the first 30 amino acids, but have different functions: α-actin is associated with contractile structures such as muscle, while β- and γ actins tend to predominate in non-muscle cells. Alpha actin tends to be the most studies and is preferred in the methods and compositions of the invention. For purposes of the present invention, any of the actin isoforms can be used, since all polymerize and can be nucleated by known nucleating agents.

Actin is a globular protein with two lobes and a deep cleft, the ATPase fold, where $Mg^{+2}$ and ATP bind. As a globular monomer, actin is known as G-actin. G-actin readily polymerizes into a two stranded filament. The polymerized form is known as filamentous actin, or "F-actin." The initiation of polymerization requires the presence of ATP. See, Dayel et al., *Proc Natl Acad Sci USA.* 18:98(26):14871–6 (2001).

There is an actin monomer concentration, known as the Critical Concentration, or "CC," below which actin will not polymerize and preassembled actin filaments will depolymerize. At monomer concentrations above the CC, the actin will polymerize until the free monomer concentration is equal to the CC. The CC values of muscle and non-muscle actin differ, and are known in the art.

The extent of actin polymerization in vitro depends upon the conditions used. When ions are added to a solution of G-actin above its critical concentration, in the presence of ATP and $Mg^{+2}$, G-actin will polymerize into a chain of F-actin molecules. When the concentration of G-actin falls below the critical concentration, assembled F-actin will depolymerize. Thus, the polymerization of actin is reversible. For example, at 4° C., muscle actin has a CC of 0.03 mg/ml in the presence of $Mg^{+2}$ (2 mM) and KCl (50 mM), but when these ions are absent, the CC is greater than 3.0 mg/ml. Thus, by altering the ionic type and strength one can alter the amount of polymer formed. Some practitioners believe that non-muscle muscle actin has its own CC values. For example, at 4° C. in the presence of $Mg^{+2}$ (2 mM) and KCl (50 mM) the CC is approximately 0.15 mg/ml. If $Mg^{2+}$ and KCl are replaced with $Ca^{2+}$, the CC will decrease to nearly 10 mg/ml. Finally, the CC of non-muscle actin can be reduced to 0.03 mg/ml by increasing the temperature to 30° C. The CC for any particular actin of choice can be readily determined for any particular set of ionic strength and temperature a practitioner wishes to consider by assays standard in the art.

Nucleating Agents

As noted, actin polymerization can be initiated through either an Arp2/3 complex-dependent pathway, or through Arp2/3 independent pathways. Agents that initiate actin polymerization through the Arp2/3 complex dependent pathway change the conformation of Arp2/3 complex to resemble an F-actin dimer and are more properly indirect nucleation agents, while agents that act through an Arp2/3 complex-independent pathway are direct nucleating agents. For ease of reference, however, both types of agents are referred to herein as "actin nucleating agents".

The exemplar of agents that act through the Arp2/3 complex pathway is the bacterial protein known as ActA, a gene product of the bacteria *Listeria monocytogenes*. See, generally, Cameron et al., *Proc Natl Acad Sci USA* 96 (9): 4908–4913 (1999); Plastino et al., *Eur Biophys J.* 33(4): 310–20 (2004). ActA facilitates actin polymerization by binding and changing the conformation of ("activating") the Arp2/3 complex, which then serves as a filament nucleus.

Other bacterial proteins that activate the Arp2/3 complex, such as IcsA (from *Shigella*) and RickA (from *Rickettsia*), which can also be used as nucleating agents, (see Cossart, P., Actin-based motility of pathogens: the Arp2/3 complex is a central player. *Cell Microbiol.* 2:195–205 (2000); Gouin, E., et al., A comparative study of the actin-based motilities of the pathogenic bacteria *Listeria monocytogenes*, *Shigella flexneri* and *Rickettsia conorii. J Cell Sci.* 112:1697–708 (1999)).

In mammalian cells, actin polymerization at the plasma membrane is induced by the recruitment of proteins such as the Arp2/3 complex by WASp or SCAR. WASp, SCAR or a peptide spanning the Arp2/3 binding domain of these proteins (the VCA peptide) can be used as a nucleating agent as all of these are capable of facilitating Arp2/3 -dependent filament nucleation. See, e.g., Suetsugu, S., et al., Identification of another actin-related protein (Arp) 2/3 complex binding site in neural Wiskott-Aldrich syndrome protein (N-WASp) that complements actin polymerization induced by the Arp2/3 complex activating (VCA) domain of N-WASP. *J. Biol. Chem.* 276:33175–80 (2001)). See also, Bernheim-Groswasser et al., *Nature,* 417(6886):308–11 (2002).

Formins can be used to nucleate actin polymerization in an Arp2/3 independent manner. Formins are multi-domain proteins with strongly conserved formin homology 2 ("FH2") domains. Zigmond, *Curr Opinions Cell Biol.* 16:99–105 (2004). The FH2 domain alone is necessary and sufficient to nucleate actin. Id. The FH2 domain is about 400 amino acids and acts as a dimer. Harris and Higgs, *Curr Biol* 14: R520–R522 (2004). All formins studied thus far act to polymerize actin. Pollard, T., *Dev Cell.* 6(3):312–4 (2004). If desired, the FH2 domain alone can be used as the nucleating agent.

Capture Agents

Any compound known to bind filamentous ("F") actin can be used as the actin capture agent. As noted elsewhere herein, myosin is the exemplar actin capture agent. Other compounds suitable for use as the capture agent are the non-protein fungal compound phalloidin. The various proteins, such as fascin and α-actinin, that link or cross link actin monomers can also be used as capture agents. More information about actin cross linking proteins is provided in the next section.

Actin Linking Agents

A number of proteins that cross link actin filaments are known in the art and can be used either to link actin filaments or as capture agents. The actin cross linking agents are classified in three groups, according to their actin binding domain. The Group I proteins include, in addition to fascin, EF-1 and scruin, and each protein in this group has its own actin binding domain. The proteins in Group II share a common 7 kD actin binding domain and include villin and dermatin. The Group III proteins have a pair of 24 kD actin binding domains, and include fimbrin, α-actinin, α- and β-spectrin, dystrophin, ABP120, and filamin. See, e.g., Lodish et al., *Molecular Cell Biology*, W. H. Freeman and Company, N.Y., N.Y. (2000), Table 18.1 (the Table can also be viewed on the Internet by entering "www.", followed by ncbi.nlm.nih.gov/books/bv.fcgi?rid=mcb.table.5128"). The structure and position of the actin binding domains of most of these proteins has been elucidated. Id. If desired, the binding domain of the proteins can be used in place of the intact proteins, particularly for use as a capture agent, since what is useful for the capture agent is the ability to bind actin and not other biological activities or functions that the intact protein might otherwise possess.

Stopping Actin Polymerization

Actin polymerization will continue as long as a solution is present containing the ingredients necessary for polymerization, such as ATP and a critical concentration of G-actin monomers. Actin polymerization can be stopped when desired by any of a variety of methods. In some embodiments, the polymerization solution containing the polymerization components is removed from the filament. For example, the solution can be drained, allowed to run off, or suctioned off, leaving the actin filament to dry. Drying is usually considered disadvantageous for proteins as it denatures them. It does not, however, affect the utility of the filament to serve to mask the surface under the filament, and therefore can be used in the methods of the invention to stop polymerization when desired.

In another group of embodiments, a fixative is added to the solution to stop the polymerization. A number of suitable fixatives are known in the art. Conveniently, the fixative is formaldehyde. The fixative can be added to the polymerization solution or the polymerization solution can be removed and replaced with a solution containing the fixative. Where the fixative is formaldehyde, the standard in the art is to use a 3.75% solution, but higher or lower amounts, for example, 2% to about 20% can be added as desired so long as the amount is sufficient to stop the polymerization reaction.

The fungal toxin phalloidin can also be used to terminate polymerization. Since phalloidin is a toxin to humans, it should be handled with care. The amounts needed, however, are quite small and with proper handling, is safe to use.

Depolymerizing Actin Filaments

Once an actin filament has been formed, it can be depolymerized if desired by contacting it with a solution comprising a protein such as gelsolin or ADF/cofilin that is known to have actin depolymerizing activity. Recombinant human plasma gelsolin is commercially available from, for example, Biogen Idec (Cambridge, Mass.). Recombinant ADF/cofilin is known in the art. See, e.g., Moriyama et al, *J Biol Chem* 267:7240–7244 (1992); Moriyama and Yahara, *EMBO J*, 18:6752–6761 (1999); Moriyama and Yahara, *Biochem J.* 365(Pt 1):147–55 (2002).

Microdisks

We have discovered that polystyrene, usually available as microspheres, can be shaped into microdisks, which have surfaces that are relatively flat. The microdisks can be manufactured from microspheres, such as polystyrene microspheres. The microspheres are subjected to pressure and heat (approximately 90° C.) to transform them into disks. If desired, the disks can be cooled while still under compression to reduce their reformation into spheres, alternatively, if it is not important that some of the disks reconvert to spheres, the disks can be cooled after the compression is relieved. When applied to conventional polystyrene microspheres, the combination of pressure and heat results in microdisks of several microns in diameter and less than one micron in height.

In one embodiment, the microdisks can be made by using a screw press. Preferably, the screw press is made out of a material that heats rapidly, such as a metal. For example, satisfactory results have been achieved using aluminum. The press can further be held in place to prevent movement or rotation.

In a preferred technique, the press is preheated before introducing the microspheres. The microspheres can conveniently be pipetted in solution onto a glass slide and spread evenly. The slide is heated so that the liquid solution evaporates, leaving the microspheres on the slide surface. Another slide is placed on top to form a "sandwich." The sandwich is placed on the press, which is then used to apply pressure to the "sandwich." The apparatus can then be cooled while the microspheres are under compression, or the "sandwich" can be removed from the press. The slides forming the sandwich can then be placed in liquid and scraped or sonicated to release the disks into the liquid. The liquid can then be centrifuged, for example at 10,000 g, to concentrate and recover the disks. Preferably, the centrifuge tubes are coated with bovine serum albumin, non-fat milk, or another inactive protein prior to introducing the disks to prevent the disks from adhering to the tubes.

EXAMPLES

Example 1

This Example shows how to make point-to-point connections using actin filaments.

A clean glass surface is made resistant to actin binding by bathing in a solution 2 mg/ml solution of bovine serum albumin ("BSA") in distilled in TE (10 mM Tris, 1 mM EDTA, pH 7.5 prepared in distilled, deionized water ("DDI")) for 30 minutes at room temperature (see Rock et al., 2000, *Methods*, 22:373–81). After blocking, the coverslip is washed 3× with TE. A row of 20 small squares is generated in the BSA 'lawn' by forcibly removing BSA by dragging the tip of an atomic force microscope probe in contact mode across the glass in ~10 nm×10 nm squares (see Wadu-Mesthrige et al., 2001, *Biophys J*, 80:1891–1899). The centers of these squares are spaced 50 microns apart. The surface is then exposed for 2 minutes to a second solution containing 10 nM of the yeast formin Cdc12 (see Zigmond, 2004, *Current Opinion in Cell Biology*, 16:99–105) in TRIS. Under these conditions, only a single formin molecule can adsorb to an exposed silica square, but some of the patches do not bind a formin. This surface is washed 3× with TE to remove unbound formin, blocked with a second round of exposure to BSA as above, and washed again 3× with TE. A second row of squares with 50 micron spacing is generated 5 microns away from the first. The surface is bathed in a solution of 10 nM N-ethylmaleimide (NEM) treated myosin (see Amann and Pollard, 2001, *PNAS*, 26:15009–15013) so that only one molecule of myosin on average is adsorbed in each of the second set of squares. This surface is washed 3× with TE to removed unbound myosin. The surface is now immersed in a solution of 0.25 uM actin (0.01 mg/ml) in Buffer B (0.15 M KCl, 5 mM $MgCl_2$, 0.1 mM EGTA, 0.5 mM ATP, 10 mM TRIS, 0.5 mM betamercaptoethanol (BME), pH 7.5). Assuming a growth rate ~20% of normal actin (see Zigmond, supra), the reaction takes 15 minutes for filaments to be 5 microns long on average. Between 12 and 18 minutes after the initiation of the reaction, some actin filaments bind to their corresponding myosin molecule as their ends diffuse over the surface. At 18 minutes the reaction is terminated by transferring the surface to a solution of 3.75% formaldehyde in Buffer B.

Example 2

This Example relates to connecting points to points with actin columns directed by.

A clean silicon surface is stamped using a PDMS stamp prepared by standard methods for contact printing (see, e.g., Tien et al., *PNAS*, 99:1758–1762 (2002)). The non-regressed regions of the stamp form a single 200 nanometer×200 nanometer square. The stamp is inked with 2 mg/ml ActA in TE (see Example 1) and pressed against the glass slide to create a nucleation site. The stamp is washed and inked with 2 mg/ml NEM-myosin to place a capture site 15 microns away from the site at which the ActA has been placed. The surface is washed 3× in TE and blocked for non-specific actin binding by immersion in 2 mg/ml BSA (see Example 1).

After blocking, the surfaces is again washed in TE and used as the floor of a flow cell that permits microscopic observation and fluid exchange (see, e.g., Amann and Pollard, *PNAS*, 98:15009–15013 (2001)). The flow cell containing TE is placed on an inverted microscope equipped with (a) a 200 mW 488 nm laser focused just above the coverslip, and (b) a stage that allows the sample to move relative to the laser focus. A TE solution filling the chamber is replaced with an actin motility mixture (see, Schwartz et al., *Current Biology*, 14:1094–1098 (2004)), that has been supplemented with a dilute solution ~0.001% w/vol 2 micron polystyrene beads passively coated with NEM-myosin (following procedures used for BSA coated beads found in McGrath et al., *Biophys J.*, 79:3258–66 (2000)).

As the naturally bundled column of actin filaments emerges from the ActA patch, an optically trapped bead is guided to the distal end of the column by sliding the stage, permitting the bead to attach to the column. Once the bead is attached, the column is placed under tension by and gently guided toward the NEM-myosin patch as it grows. It is understood that the optically trapped bead remains "trapped" in place; thus, once the bead attaches to the column, pressure can be exerted on the column by moving the stage in the direction opposite to that in which it is desired that the column go. Once contact between the column and the capture site is made the reaction is stopped and stabilized by exchanging the motility mixture with a solution containing 10 uM solution of phalloidin in Buffer B (see Example 1).

Example 3

This Example provides a discussion of how to form a vertical array of equally sized biocolumns.

Two clean glass coverslips (~25 mm square) are prepared with an array of 100 nm×100 nm squares by contact printing (see Example 2). On one surface, ActA molecules are patterned in the squares, while on the second surface NEM-myosin molecules are patterned on the squares. Each uncoated surface of coverslip is held in a micropipette device by negative pressure (see, for example, Waugh et al., *Blood*, 97:2720–2739 (2001)). The micropipettes are mounted on micromanipulators that allow the patterned surfaces to be brought in contact and aligned. The positioning takes place within a small fluid chamber under an inverted microscope (see, Waugh et al., supra, for discussion of chamber and manipulation techniques). The fluid chamber, filled with TE so as not to dry the patterned proteins, is exchanged for motility media (see Example 2) to initiate column growth from the nucleating plate. Once nucleation begins, the binding plate is moved away from the nucleating plate at a rate of approximating the rate of column growth but not faster (typically this will be 0.1 micron/min, see Schwartz et al. *Current Biology*, 14:1094–1098 (2004)). Columns clearly extend between the plates and are terminated at any desired height by introduction of 10 uM capping protein, and 10 uM phalloidin in Buffer B. The capping protein liberates the columns from the nucleating plate as these are bound at their barbed ends and the phalloidin stabilizes the columns against depolymerization.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising a surface having disposed thereon (a) an actin nucleation site comprising an isolated actin nucleating agent and (b) an actin capture site comprising an isolated actin capture agent, with a space between said actin nucleating site and said actin capture site, wherein said actin nucleation agent is selected from the-group consisting of ActA, IscA, RickA, a VCA domain, WASp, a formin, and a formin FH2 domain,and wherein said actin capture agent is selected from the group consisting of myosin, N-ethylmaleimide-myosin, phalloidin, .alpha.-actinin, and fascin.

2. A composition of claim 1, further comprising a plurality of addressable actin nucleation sites and a plurality of addressable actin capture sites.

3. A composition of claim 1, further comprising at least one actin filament connecting said actin nucleation site to said actin capture site.

4. A composition of claim 2, further comprising at least one actin filament connecting at least one actin nucleation site to at least one actin capture site.

5. A composition of claim 1, wherein said surface is a planar surface.

6. A composition of claim 1, wherein said surface is silicon, strained silicon, polycrystalline silicon, polycrystalline silicon, silicon dioxide, germanium, gallium arsenic, glass, plastic, ceramic, or metal.

7. A system comprising a surface having disposed thereon (a) an actin nucleation site comprising an isolated actin nucleating agent and (b) an actin capture site comprising an isolated actin capture agent, with a space between said actin nucleating site and said actin capture site, wherein said actin nucleation agent is selected from the-group consisting of ActA, IscA, RickA, a VCA domain, WASp, a formin, and a formin FH2 domain, and wherein said actin capture agent is selected from the group consisting of myosin, N-ethylmaleimide-myosin, phalloidin, .alpha.-actinin, and fascin.

8. A system comprising a first and a second surface, with said first surface having disposed thereon an actin nucleation site comprising an isolated actin nucleating agent and said second surface having disposed thereon an actin capture site comprising an isolated actin capture agent, wherein said system further comprises at least one actin filament connecting said actin nucleation site on said first surface with said actin capture site on said second surface, wherein said actin nucleation agent is selected from the-group consisting of ActA, IscA, RickA, a VCA domain, WASp, a formin, and a formin FH2 domain, and wherein said actin capture agent is selected from the group consisting of myosin, N-ethylmaleimide-myosin, phalloidin, .alpha.-actinin, and fascin.

9. A system of claim 8, wherein said first surface and said second surface are positioned parallel to each other.

10. A method of connecting a pair of points separated by a space on a surface, said method comprising (a) contacting a first point of said pair with an isolated actin nucleation agent; (b) contacting a second point of said pair with an isolated actin capture agent; (c) contacting said isolated actin nucleation agent at said first point with a polymerization solution, which solution comprises ingredients sufficient to induce and to maintain actin polymerization, thereby inducing polymerization of an actin filament; and (d) permitting said polymerization of said actin filament to continue until said actin filament contacts said actin capture agent at said second point, thereby connecting said first and second points, wherein said actin nucleation agent is selected from the-group consisting of ActA, IscA, RickA, a VCA domain, WASp, SCAR, a formin, and a formin FH2 domain, and wherein said actin capture agent is selected from the group consisting of myosin, N-ethylmaleimide-myosin, phalloidin, .alpha.-actinin, and fascin.

11. A method of claim 10, wherein said method further comprises immersing said first point, said second point, and said space between said points with said polymerization solution at the same time.

12. A method of claim 10, wherein said method further comprises removing said polymerization solution following said contacting of said actin filament to said second point.

13. A method of claim 10, wherein said method further comprises adding a fixative to said polymerization solution following said contacting of said actin filament to said second point.

14. A method of claim 10, wherein said surface is coated with a non-stick coating before contacting said actin nucleation agent on said first point with polymerization solution.

15. A method of claim 10, further comprising a plurality of pairs of points on said surface.

16. A method of claim 15, wherein said plurality of pairs of points on said surface are arranged in an addressable array.

17. A method of claim 10, further wherein said surface is contacted with an etching solution following formation of said actin filament.

18. A method of claim 10, further wherein a particle is attached to said polymerizing actin filament to permit a force to be exerted to direct said filament towards said actin capture agent.

19. A method of claim 18, further wherein said particle is a magnetic particle.

20. A method of claim 19, further wherein a magnetized substance is positioned near said magnetic particle so as to draw said magnetic particle towards said actin capture agent.

21. A method of claim 18, further wherein said particle is a transparent or translucent particle.

22. A method of claim 18, wherein said force directing said filament towards said actin capture agent is optical gradient pressure.

23. A method of claim 10, further wherein said polymerizing actin filament is directed towards said actin capture agent by liquid flowing toward the actin-capture agent.

24. A method of claim 10, wherein said surface is silicon, strained silicon, polycrystalline silicon, polycrystalline silicon, silicon dioxide, germanium, gallium arsenic, glass, plastic, ceramic, or metal.

25. A method of claim 10, wherein said surface is planar.

26. A method of forming a three dimensional actin structure, said method comprising: (a) providing a first surface having a first point, which first point has thereon an actin nucleation agent and a second surface having a second point, which point has thereon an actin capture agent, and further wherein said first and said second surfaces are positioned so as to create a space of up to 10 microns between said surfaces; (b) filling the space between said first point on said first surface and said second point on said second surface with a polymerization solution, which solution comprises ingredients permitting induction and maintenance of actin polymerization, thereby inducing polymerization of an actin filament; and (c) permitting said polymerization of said actin filament to continue until said actin filament contacts said actin capture agent at said second point, thereby connecting said first and second points; thereby creating a three dimensional structure, wherein said actin nucleation agent is selected from the-group consisting of ActA, IscA, RickA, a VCA domain, WASp, SCAR, a formin, and a formin FH2 domain, and wherein said actin capture agent is selected from the group consisting of myosin, N-ethylmaleimide-myosin, phalloidin, .alpha.-actinin, and fascin.

27. A method of claim 26, further wherein said first and second surfaces are positioned parallel to each other.

28. A method of claim 26, further comprising a plurality of points on said first surface to be connected to a plurality of points on said second surface.

29. A method of claim 27, further comprising a plurality of points on said first surface to be connected to a plurality of points on said second surface.

30. A method of claim 26, further comprising separating said first and second surfaces to exert a tension on said actin filament until a desired separation between said surfaces is achieved.

31. A method of claim 26, wherein said surfaces are independently selected from the group consisting of silicon, strained silicon, polycrystalline silicon, polycrystalline silicon, silicon dioxide, germanium, gallium arsenic, glass, plastic, ceramic, and metal.

32. A method of claim 26, further wherein a particle is attached to said polymerizing actin filament to permit a force to be exerted to direct said filament towards said second site on said second surface.

33. A method of claim 32, wherein said particle is magnetic and the force directing said particle towards said second site is magnetism.

34. A method of claim 26, further wherein said actin filament is released from said first surface by contacting said filament with capping protein.

* * * * *